United States Patent [19]

Lee et al.

[11] 4,312,219
[45] Jan. 26, 1982

[54] APPARATUS FOR MEASURING HOT SURFACE DRYING RATE OF LIGHT WEIGHT POROUS MATERIALS

[75] Inventors: Peter F. Lee, Auburn; Jeffrey A. Hinds, Sumner, both of Wash.

[73] Assignee: Weyerhaeuser Company, Tacoma, Wash.

[21] Appl. No.: 128,600

[22] Filed: Mar. 10, 1980

[51] Int. Cl.³ .............................................. G01N 5/04
[52] U.S. Cl. ...................................................... 73/76
[58] Field of Search .................... 73/15 B, 76; 34/151, 34/239; 73/15R

[56] References Cited

U.S. PATENT DOCUMENTS 1,089,826  3/1914  Emerson .................................. 73/76
3,055,206  9/1962  Watson et al. ...................... 73/76 X

OTHER PUBLICATIONS

Dreshfield, Jr.-"Hot-Surface Drying of Fibrous Sheets"-*Chem. Eng. Prg.*, 53(4):174 (1957).
Kirk, et al.-"Hot Surface Drying of Paper", *Paper Technology*, 11(5):347 (1970).
Sherwood-"The Drying of Solids-II"-*Ind. Eng. Chem.*, 21(10):976 (1929).
Smith, et al.-"Paperboard Drying Investigation by Means of an Experimental Drying Machine," *TAPPI*, 36(11):481 (1953).

*Primary Examiner*—Charles A. Ruehl

[57] ABSTRACT

An apparatus that is capable of continuously measuring the weight loss of a light weight, porous sheet material during drying while in constant contact with a heated surface. The resulting data may be converted to drying rate curves suitable for analyzing the effects on drying rate of furnish additives and processing conditions. The testing device is particularly useful for evaluating grades of paper or paperboard having basis weights greater than 50 g/m². The device includes an electrically heated arcuate plate maintained at a constant temperature. The paper sample to be tested is brought into good heat transfer contact with the plate by means of a tensioned fabric that exerts a normal load on the sample but does not interfere with mass transfer of the vapor away from the drying sample. An air ventilating system provides a low turbulence flow of air uniformly over the fabric covering the sample. The plate, sample and fabric are supported by a load sensor that measures changes in weight of the sample during drying to 0.01 g. A special electrical connector between the power source and the heating elements of the hot plate isolates the power source from interference with the weighing measurement. Current is supplied to mercury pots, independently supported of the hot plate. Probes mounted on the hot plate and connected to the plate heating elements partially submerge in the mercury pots, transmitting power to the plate.

7 Claims, 5 Drawing Figures

APPARATUS FOR MEASURING HOT SURFACE DRYING RATE OF LIGHT WEIGHT POROUS MATERIALS

BACKGROUND OF THE INVENTION

1. Field of the Invention

The field of the invention is the drying of porous materials such as textiles, paper and paperboards, certain foods and the like. More particularly, the subject of this invention is a drying rate testing apparatus capable of relating laboratory results to actual mill operations.

2. Prior Art

Papermaking is a capital intensive process and there is an appreciable economic incentive to increase utilization of this capital through increased productivity. The production rates on many paper machines, particularly among those producing heavy grades of paper or board, are limited by the rates at which water can be removed from the wet paper webs by evaporation. In these situations, it is common to minimize the evaporative load on the dryer by adjusting process and furnish variables, within the constraints of product quality, to enhance water removal by mechanical processes such as drainage or pressing. However, the effects that the properties of a wet web, such as composition and structure, have on the evaporation rates within the dryer can be appreciable. These effects should not be overlooked, but have in the past been difficult to predict because of limitations of the analytical techniques.

Most of the paper and board produced commercially is dried by threading a continuous wet web around each of a series of rotating, steam heated cylinders. The cylinders are generally arranged so that the wet web spends approximately 80% of the drying time in contact with the heated cylinders and approximately 20% of the drying time between cylinders in open draws. Almost all of the heat required for vaporization is transferred into the sheet during contact with the hot cylinder and the overall drying rate is directly dependent upon the overall resistance to heat transfer during contact. Any change in this resistance will be manifested as a corresponding change in the overall drying rate.

The overall resistance of the transfer of heat from steam to paper during contact is the sum of the resistances due to the condensing layer on the inside surface of the cylinder, the cylinder walls, the contact between the cylinder and the web, the paper web itself and the boundary layer of air adjacent to the open surface of the web. The open-mesh dryer fabrics normally used with most dryers offer negligible resistance to the transfer of heat.

It can be shown, in all but the lightest grades of paper, that the transfer of heat is limited primarily by the contact resistance and the internal resistance of the paper or board. It has been estimated that the sum of these two resistances typically accounts for between 50 and 90% of the total resistance to heat transfer in paper and paperboard grades.

Drying of a wet web is a complex process involving the concurrent and interactive flow of heat and mass through a structure which is itself responding to local changes in moistures and moisture gradients. This complexity is manifested in the complex dependence of the overall thermal resistance of the web to factors such as web composition and structure, drying conditions and drying history.

Elaborate models have been proposed to qualitatively describe the phenomenon of heat and mass transport within the sheet during prolonged contact with the hot dryer surface. However, present knowledge is generally inadequate to predict the magnitude and often even the direction of changes in drying rate on a drum dryer due to changes in process or furnish variables.

It has been shown that during prolonged contact with a hot plate, evaporation occurs from regions of the web close to both the open and closed surfaces. In heavy grades of paper and paperboard, distinct concentration gradients form through the thickness of the web with most of the water located in regions remote from both surfaces. This distribution of water more or less resembles the symmetrical distribution of moisture which must exist within a web during conventional drum drying, when both surfaces are alternatively exposed to either a hot surface or a drying atmosphere. The mechanisms controlling heat and mass transfer are, therefore, expected to be the same in both systems.

Though the economic stake in improving drying production is high, a practical analysis of the heated surface drying of thin porous sheets has not yet come to fore. The relatively small changes in weight of the wet paper during drying have been difficult to accurately measure because of the typically heavy hot metal surface on which they are dried. Discontinuous measurement of change of weight of these kinds of samples during drying has, in general, yielded results of only limited usefulness because of insensitivity of the measuring techniques or a failure to control important process variables. Attempts to obtain significant correlation between lab results and mill processes have largely failed because of the difficulty of measurement.

T. K. Sherwood in "The Drying of Solids-II," Ind. Eng. Chem. 21(10):976 (1929) describes drying slabs of 1.52 cm thickness of sulfite pulp using a stream of hot air while using a recording balance to continuously measure weight change versus time. Since no heavy hot plate was used, the total weight to be measured permitted accurate measurement. However, air drying of wood pulp involves the countercurrent flow of heat and mass within the porous structure. Drying characteristics under these conditions do not resemble those of hot surface drying which involves the cocurrent flow of heat and mass. Consequently, results from air drying experiments have not been useful for predicting drying rates on drum dryers.

Smith and Attwood in "Paperboard Drying Investigation by Means of an Experimental Drying Machine," TAPPI 36(11):481 (1953) describe a complex mechanical device that is an attempt to simulate all phases in a conventional drum dryer. The maximum simulation speed of 240 ft per minute is low in comparison with real paper machine speeds. The simulation also fails with respect to determining drying rates because the method for measuring moisture content is discontinuous and therefore imprecise.

Dreshfield in "Hot Surface Drying of Fiber Sheets," Chem. Eng. Prg. 53(4):174 (1957) describes a beta ray transmission method for measuring the moisture content of fibrous webs on a hot plate. Moisture measurements are discontinuous and only vaguely describe the drying rate. As an alternative to more conventional techniques, the beta ray method is complicated and expensive and, therefore, impractical.

Kirk and Jones in "Hot Surface Drying of Paper," Paper Technology 11(5):347 (1970) describe a technique for measuring drying rate of a hot surface dryer, in which the wet sheet was intermittently separated from the hot surface, weighed and returned to the hot surface. While producing drying rate curves, the inaccuracy of the determination is particularly evident in the "falling rate" portion of the curves.

SUMMARY OF THE INVENTION

It is an object of the invention to provide an apparatus that permits the accurate and continuous measurement of drying rates of lightweight, thin porous media, particularly thin sheets of paper and paperboard. The resulting drying rate data permit correlation of laboratory results with drying on a paper machine cylinder drying section. Thus, one may predict from laboratory measurements how different furnishes and additives will affect drying in the full-scale mill operations.

The apparatus is capable of continuously measuring the weight of a sample during drying. The sample, during the measuring process, rests on a plate having a heat transfer surface and heating means for maintaining the heat transfer surface at a constant uniform temperature. A permeable fabric means ensures that the sample of porous material is in good heat transfer contact with the plate. The fabric is of such construction that it does not substantially impede mass transfer from the drying sample. A latching mechanism of the fabric means causes the fabric to exert a normal force on the sample, pressing it into contact with the hot plate. An air delivery means provides a low turbulence flow of air, of constant temperature and humidity, uniformly over the surface of the fabric means. A load sensor means, for weighing continually the changes in weight of the sample while it is heated on the plate, supports the hot plate, the sample and the fabric means, independently of any forces not related to the weight loss of the material.

In a preferred embodiment, the porous material of interest is paper or paperboard having a basis weight greater than about 50 g/m$^2$. In this embodiment the hot plate means is arcuate and provided with electrical heating means. The fabric is a flexible open mesh synthetic drying fabric with a lever latch means for tensioning the fabric to conform the fabric to the plate means to insure heat transfer contact of the sample with the plate. The tensioned fabric means exerts a normal force or load on the paper sample, substantially duplicating what occurs on drying cylinders wrapped with fabric designed to force or hold the paper web into good thermal contact with the cylinder drying surface.

An electrical heating means, including plate heating elements, produces a constant uniform heat transfer surface temperature. An electrical connector means connecting a power source and the plate heating elements is designed to isolate the weighing process from drag forces of wires and the like that would otherwise cause inaccuracies in measuring weight changes during drying of the thin, lightweight samples. The electrical connector means comprises a container of mercury supported independently of the heated plate. An electrical means establishes a flow of electrical current from the power source to the mercury. A probe means supported on the heated plate is insulated therefrom but connected by electrical means to the heating elements and partially submerged in the mercury. The power source transmits electrical current to the mercury which is transmitted through the probe means to the heating elements.

An air delivery system is designed to provide a flow of air across the surface of the fabric means to remove moisture as it is driven from the sample of interest during drying by the heat of the hot plate. A plurality of inlet tubes helps reduce the scale of turbulence in the air flow across the surface of the fabric means. A ventilator hood means conforms to the curvature of the hot plate and fabric means, providing sufficient clearance for the air flow to pass uniformly over the surface of the fabric means. The air is of sufficient bulk velocity such that changes in humidity of the air in passing over the sample remain negligible.

DESCRIPTION OF THE PREFERRED EMBODIMENT

Figure 1:
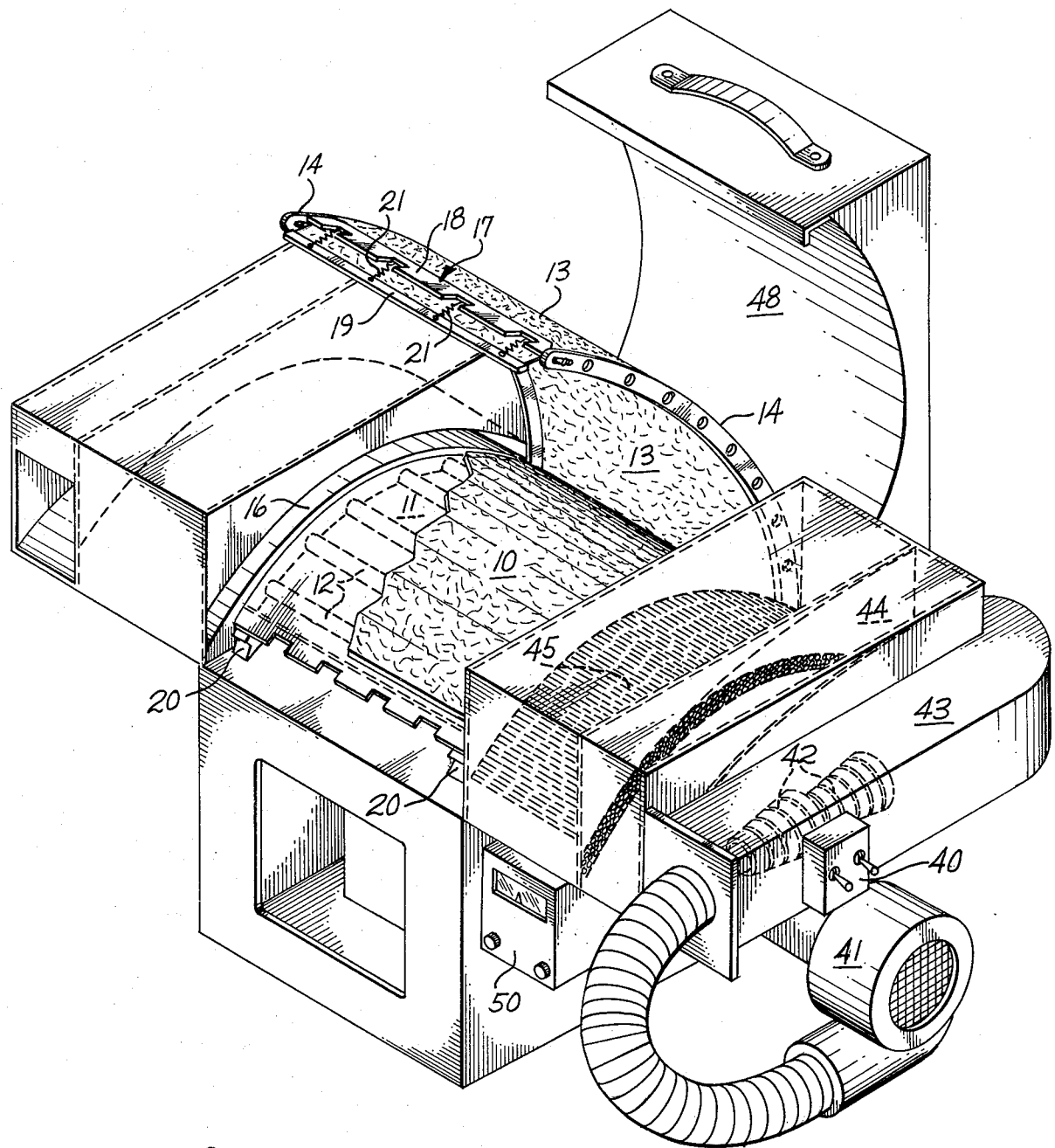
FIG. 1 is an isometric projection of an embodiment of the apparatus with the ventilator hood and fabric means in the open position.
Figure 2:
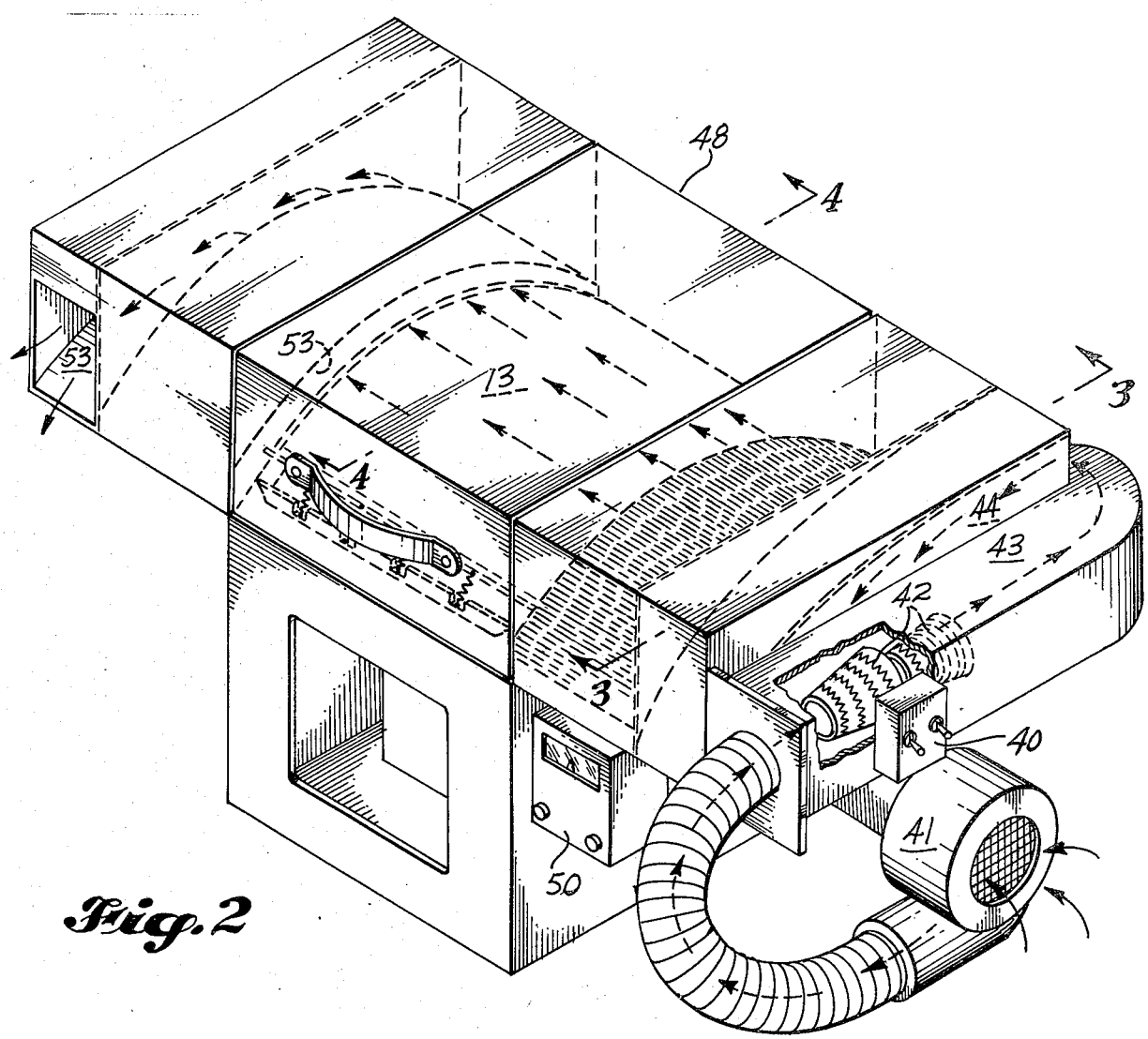
FIG. 2 is a similar view showing air flow over the fabric means and sample during operation.

The apparatus of the invention is capable of accurately and continuously measuring the instantaneous drying rate of lightweight porous material such as paper, paperboard, textiles and certain foods in contact with a hot surface. The material to be tested is held against a metal hot plate by means of a permeable, thermally stable fabric. The hot plate and sample are connected to a load sensing device by means of a non-conductive shaft. Changes in weight of the sample are measured and recorded continuously as a function of time. These measurements may then be translated into terms of "drying rate" as a function of moisture content.

Referring to FIGS. 1–4, a preferred embodiment of the drying rate tester is depicted. A sample 10 of relatively thin porous paperboard having a basis weight greater than about 50 g/m$^2$ is obtained either from a papermaking process or formed from pulp into a handsheet in the laboratory. The sample 10 is cut somewhat smaller than the dimensions of a hot plate 11 shown in FIG. 1 in isometric view and in FIG. 4 in a sectional elevation. The hot plate 11 is arcuate in shape in this configuration, substantially representing a portion of the surface of a paper machine drying cylinder. The hot plate is of hollow construction containing cylindrical heating elements 12 immersed in a heat transfer fluid such as ethylene glycol. With this system, uniform surface temperature, a relatively large heat capacitance and a minimum total weight are achieved. The temperature of the hot plate may be adjusted and is automatically controlled by thermostat 50 during testing. A drying fabric 13, somewhat smaller in size than hot plate means 11, is provided with frame members 14 which are supported at pivots 15 mounted on the hot plate surface 11 such that fabric 13 may be lowered onto hot plate 11, pressing the sample 10 into heat transfer contact with hot plate 11. The frame members 14 of fabric 13 fit flush at the edges 16 of heating plate 11 and flush with the top portion of the heat transfer surface of the plate 11.

A latching mechanism 17 is provided to tension the fabric in the direction of curvature in order to firmly hold the sample against the hot surface.

The latching mechanism 17 comprises a latching bar 18 pivoted at each end between fabric frame members 14. The fabric, which comprises an open mesh synthetic similar to that found in production dryer units, terminates in a load distributing bar 19. Springs 21 connect the fabric bar 19 to latching bar 18. Two receiving elements 20 are provided on the hot plate 11 for receiving the ends of latching bar 18. The ends of latching bar 18 are inserted in elements 20 and the bar 18 rotated downwards, tensioning the springs 21, and hence, bar 19, thereby exerting a normal force on the sample contained between the surfaces of the fabric and the heat contact surface of the hot plate 11.

Figure 4:
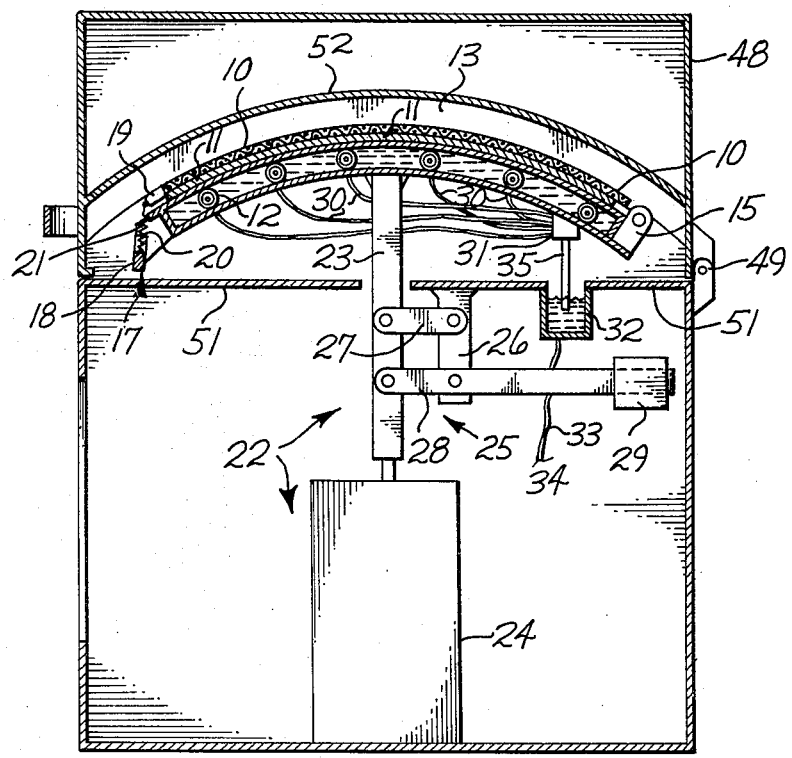
FIG. 4 is a section along lines 4—4 of FIG. 2 showing the hot plate and load sensor means of the apparatus.

As shown in FIG. 4, hot plate 11, sample 10 and fabric means 13 are supported by load sensor means 22. The load sensor means 22 consists of a supporting column 23 connected to a load sensing device 24 of appropriate sensitivity. The arrangement 22 is capable of detecting the relatively small weight changes occurring in the sample 10 while the sample remains on the electrical heating plate 11 as drying takes place.

Any load sensing device 24 of appropriate sensitivity is suitable, such as a digital balance 24 with a sensitivity of 0.01 grams. The output of the balance may be connected to a microprocessor-based data acquisition system which permits the storage and subsequent automatic analysis of the drying rate data.

Some of the weight on the balance is offset by means of counterbalance mechanism 25 which includes a support element 26 mounted on apparatus framework 51, independent of the hot plate means 11. A link 27, pivoted at both ends, connects the column 23 with the supporting element 26. Lever arm 28 is pivoted from support column 23 and 26 and has an adjustable weight 29 on the end thereof which can be adjusted to offset, as desired, a portion of the total weight of the hot plate sample and fabric means, thereby improving the sensitivity of the test.

Further improving the sensitivity of the apparatus is an electrical connector system that eliminates drag forces that would ordinarily act on the measuring system if ordinary electrical wire connecting means were used between the power source and the hot plate means. Heating means for hot plate 11 includes electrical connector means 30 connecting heating elements 12 to junction box 31. A mercury pot 32, containing a quantity of mercury, is supported on the apparatus framework 51. An electrical connector means 33 transmits electrical current from a power source 34 (not shown) to the mercury in the pot 32. During operation of the apparatus, electrical current is transmitted to heating elements 12 through a probe 35, connected to box 31, which probe 35 remains partially submerged in mercury pot 32.

Figure 3:
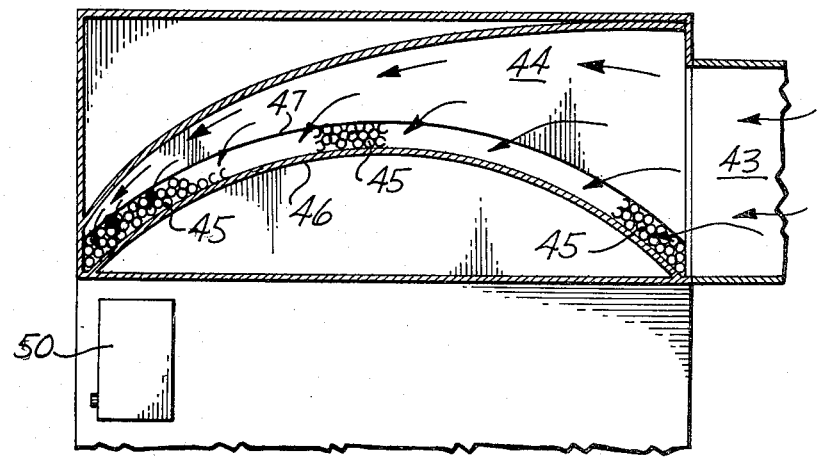
FIG. 3 is a section of FIG. 2 along lines 3—3 of FIG. 2 showing inlet air baffling.

The drying tester apparatus is provided with an air ventilating system 40 which consists of an air blower 41 blowing air through duct 43. Heaters 42 increase the temperature and reduce the relative humidity of the air flowing through the instrument. As shown in FIG. 3, the air flow is directed into chamber 44 and therefrom through deflector tubes 45 comprising ⅛" diameter tubes of about 6" length. The tubes 45 are held in parallel alignment by wall 46 and upper wall 47 such that the bottom of the tubes are in alignment with the top surface of fabric 13.

A wind tunnel cover 48 has an inner surface conforming substantially to the arcuate surface 11 of hot plate. The wind tunnel 48 pivots on a support 49 on framework 51 so that, when in the operational closed position, the bottom edge 52 of the cover 48 is in alignment with inlet tubes 45 providing a uniform plenum across the entire surface of the fabric 13. Discharge chamber 53 allows air to exit the testing apparatus.

The air system is designed to provide a flow of constant temperature and low humidity air over the surface of fabric 13 to remove water vapor as it evaporates from the sample on heated plate 11. Sufficient velocity of air is provided so that changes in humidity of the air stream during drying are negligible. The tubes 45, their alignment and tunnel cover 48 are designed so that there is a uniform flow of low turbulence air over the surface of the fabric.

In operation, a paper or paperboard sample is obtained from a paper machine, typically at the press section, or made up from pulp into a laboratry handsheet. It is cut to size and placed on hot plate surface 11. Fabric 13 is then lowered onto sample 10. Latch mechanism 17 is activated to bring the sample into good thermal contact with hot plate 11 and tunnel cover 48 is then closed and secured. The hot plate and air systems are activated and measurements over time are made during the drying of the sample.

EXAMPLE

The drying rate of handsheets of a fiber furnish comprising never-before dried, unbleached Douglas fir kraft pulp with a Canadian Standard Freeness of 721 CSF (before refining) were run of the testing apparatus. The sheets were dried with their wire-side in contact with the hot surface. The sheets were 20.3 cm square when wet and had oven dried weights of $24.5 \pm 1.0$ g, corresponding to basis weights of $595 \pm 25$ g/m$^2$. Laboratory handsheets with uniform and reproducible fiber distributions were used throughout the experiments.

The hot plate upper surface was a section of a cylinder with a diameter of 50.0 cm and a projection of 625 cm$^2$ and of aluminum construction. The temperature of the hot plate was maintained at $105° \pm 0.1°$ C. by means of a closed-loop, negative feedback control system. The fabric adhering the paper sample to the hot plate was tensioned in the direction of the curvature of the plate at 7 N/cm which is equivalent to a normal load of 2.8 kPa on the wet web sample. The wet and dry bulb temperature of the inlet air was controlled at 23° and 45° C., respectively. The bulk velocity of air over the sheet was maintained at a constant 7.5 m/sec.

The changing weight of the sample during drying on the hot plate was measured by the load sinsing device which was a Mettler digital balance, Model PC 4400 manufactured by Mettler Instrument Corporation of Hightstown, N.J. The changing weight measured by the load cell was digitized at a rate of 27 samples per minute and stored on magnetic tape. A computer was subsequently used to re-express and graph these data as weight of residual water in the web versus drying time and as instantaneous drying rate versus average sheet moisture or time. Each value of instantaneous drying rate was determined by calculating the slope of the least-squares, linear, regression line which best related the weight of residual water to drying time within seven seconds either side of the point of interest and normalized by dividing by the oven dried basis weight of the web. The computer was also used to evaluate the overall drying rate as the time average of the instantaneous drying rates between any two prescribed limits of sheet moisture.

In order to measure the drying characteristics of a wet fiber web over a wide range of solids contents, the handsheets were dried in an as-formed condition, without pressing. The initial wet web solids content was 16%. Drying rate data are presented in FIG. 5, as a graph of the weight of residual water and instantaneous drying rate versus time.

Figure 5:
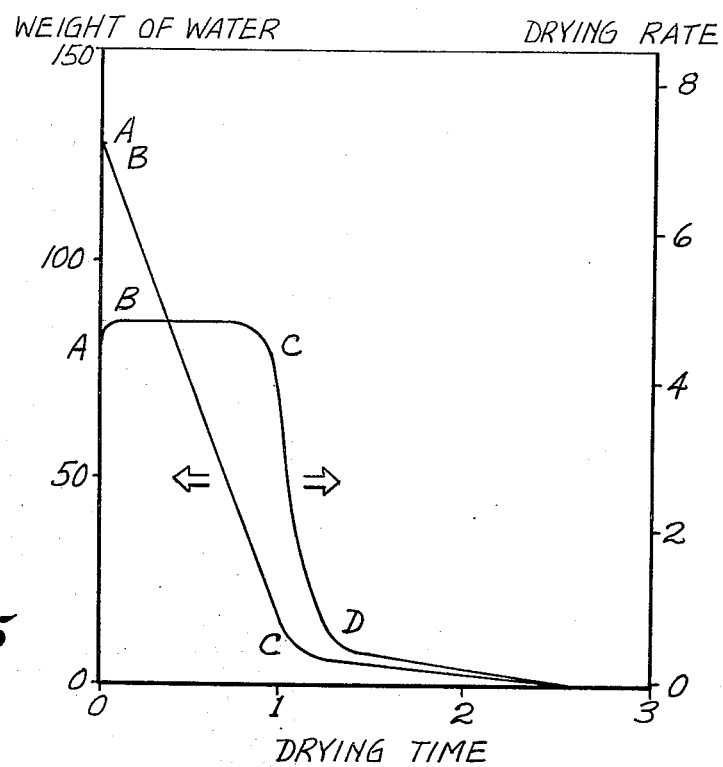
FIG. 5 is a graph of the results produced by the apparatus, including drying rate versus drying time.

Referring to FIG. 5, four distinct regimes of drying can be distinguished. Each regime is delineated by rapid changes in the drying rate.

Immediately following contact between the wet web and the hot surface, there was an initial, short warmup period, regime AB, during which drying rate increased rapidly and approached a constant value. The precise form of the drying curve during period AB is strongly dependent upon initial sheet temperature. In these experiments the sheets were preheated to 75° C. in a 100% humidity environment prior to drying, in order to minimize the duration of the warmup period.

Under the drying conditions used in this experiment, there was a well-defined regime of constant drying rate, regime BC, which persisted up to an average solid content of 55%. It is widely accepted that during the period of constant drying rate, porous structures are sufficiently moist and the internal rates of heat and mass transfer sufficiently high for the drying rates to be limited primarily by the transport phenomen within the boundary layer of air adjacent to the open surface. The drying rates in this regime should therefore depend mostly upon external variables such as the temperature, humidity and velocity of the air and to be largely independent of the mechanisms of heat and mass transfer within the sheet.

Following the constant rate period and for most of the overall drying time, the drying rate decreased continuously as the solids content increased. Two distinct falling rate periods CD and DE are apparent in FIG. 5. Prior workers have correlated point C on the drying curve, at least for a web of glass fibers, with the formation of a liquid-free region of relatively high thermal resistance adjacent to the hot surface. The formation and subsequent growth of such a dry layer would rapidly increase the internal resistance of the web and shift the controlling thermal resistance from the air boundary layer.

Beyond point C, the effects that the composition and structure of the wet web have on the transfer of heat or mass will be important. This is the portion of the drying rate phenomenon that has heretofore been largely unexamined for papers and paperboards.

During the first falling rate period CD, the drying rate decreased rapidly by a factor of 25 until at point D the average solids content of the web had increased to 85%. At solids contents higher than at point D, the decreased rate of drying may in part be explained by the increased energy required to vaporize the last traces of water bound by intermolecular and interfacial forces.

The graphical results of the above experiments and other similar tests are useful in assessing benefits predicted to be realized by changes in the forming, pressing and drying systems. For example, it has often been thought that an increased mechanical expression of water in the press section of a paper machine would be a way of gaining productivity. The measuring apparatus and system of this invention produce results that show that because of the relatively high rates of evaporation in the early stages of drying, a decrease in the initial water content of the web would have a disproportionately small effect on the total drying time. If the weight of water to be evaporated were reduced, for example, by 20% from an initial moisture content of 46 g or 35% solids to 37 g or 40% solids without adversely affecting the sheet structure, the drying time would have been reduced by only 3%. This suggests that the large increases in production resulting from increased mechanical dewatering in the presses actually measured can only partially be explained by the decrease in moisture entering the dryers. When the effects of wet pressing were tested on the apparatus of this invention, the results showed that decreasing the wet caliper from 3.00 mm to 1.52 mm increased the overall drying rate, evaluated between 45 and 95% solids, by 67%. Thus, it appears that the marked increases in commercial dryer capacities often associated with increased mechanical dewatering may, in part, be explained by the increase in drying due to decreased wet caliper. The higher drying rates in the more densified webs is probably due to the higher internal rates of heat and mass transfer, which are presumed to occur primarily as a result of corresponding increases in the internal gradients of temperature and concentration, respectively. These results indicate that structural changes in the wet web induced by web pressing may also affect drying rate.

The apparatus is capable of identifying problems with the fiber furnish itself. It can predict how a change in furnish additives, such as drainage aids and the like, will affect drying. For example, in changing from sulfite to thermomechanical pulp, the test results show a significant decrease in production, for dryer limited machines, which in fact actually was experienced in the mill. The apparatus provides a means for predicting such changes, allowing better production planning, selection of productions aids and the elimination of furnishes that are uneconomical.

The apparatus of this invention may be used to predict how a particular paper will dry on the paper machine. Its performance on the lab tester can be correlated with the full-scale mill systems. Once the drying rate of a new furnish has been reliably established, capital investments in drying for a new mill, for example, can be more reliably determined. Trial and error machine runs can be eliminated, which reduces the lost production time and wasted stock resulting from mill trials.

What is claimed is:

1. An apparatus for continuously measuring the weight of a porous material during drying on a hot surface, comprising:

a plate, having a heat transfer surface in contact with said porous material, said plate having a heating means for maintaining said heat transfer surface at a constant uniform temperature;

a permeable fabric means for adhering said porous material into heat transfer contact with said plate, without substantially impeding mass transfer from said porous material;

an air delivery means for directing a flow of air, of constant temperature and humidity, uniformly over the surface of said fabric means; and a load sensor means, for weighing continuously changes in weight of said material while said material is being dried on said plate, wherein said sensor means supports said plate, material and fabric means independently of forces not related to the weight loss of said material.

2. The apparatus of claim 1, wherein:
said plate is arcuate and provided with an electrical heating means.

3. The apparatus of claim 2, wherein said plate electrical heating means, comprises:
electrical heating element means for producing a constant uniform heat transfer surface temperature of said plate;
a power source means; and
an electrical connector means for transmitting electrical current from said source to said heating element means independently of any connecting wires which would otherwise exert drag forces on said plate causing error in the measurement of the changes in weight of said samples, said connector means comprising a container of mercury supported independently of said heated plate, an electrical means establishing a flow of power from said power source to the mercury and a probe means supported on said heated plate and connected by electrical means to said heating element means, said probe partially submerged in said mercury, wherein power impressed upon said mercury is transmitted through said probe means to said heating elements.

4. The apparatus of claim 1 wherein said fabric means comprises a flexible, open mesh synthetic fabric and a latch means for tensioning said fabric to conform said fabric to said plate means to insure heat transfer contact with said plate.

5. The apparatus of claim 4 wherein said porous sample material is paper, said plate means is arcuate in form and said fabric means exerts a normal load on said paper sample, substantially duplicating that experienced by a paper web on paper machine cylinder dryers.

6. The apparatus of claim 1 wherein said air delivery means comprises a plurality of inlet air flow dispersion tubes in parallel alignment, in the plane of the porous sample, such that there is a low turbulence, substantially laminar flow of air, distributed evenly over said fabric means, said air moving at sufficient bulk velocity such that changes in humidity of the air in passing over said sample remain negligible.

7. A method of characterizing porous cellulosic sheets having a basis weight greater than at least about 50 g/m$^2$, comprising:
adhering a sample of said cellulosic sheet to a hot plate means having;
a heat transfer surface and a means for imparting a uniform constant temperature thereto,
a permeable fabric means for adhering said porous material into heat transfer contact with said plate without substantially impeding mass transfer from said porous material,
an air delivery means for directing a flow of air of constant temperature and humidity uniformly over the surface of said fabric means, and
a load sensor means for weighing continuously changes in weight of said material while said material is heated by said plate, wherein said sensor means supports said hot plate material and fabric means independently of forces not related to the weight loss of said material;
heating said sample on said hot plate means until said sample is bone dry; and
recording, simultaneously with said heating step, the weight of said sample as it dries
wherein the rate of change of said weight with time correlates with drying rate performance of said sample in a paper machine cylinder drying machine.

* * * * *